US012122751B2

(12) United States Patent
Jiao et al.

(10) Patent No.: US 12,122,751 B2
(45) Date of Patent: *Oct. 22, 2024

(54) PROCESSES OF MAKING 2-((1-BENZYL-1H-INDAZOL-3-YL)METHOXY)-2-METHYLPROPANOIC ACID AND ITS DERIVATIVES

(71) Applicant: Translatum Medicus Inc., Toronto (CA)

(72) Inventors: Xiangdong Jiao, Toronto (CA); Kanjai Khumtaveeporn, Toronto (CA)

(73) Assignee: Translatum Medicus Inc., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/356,977

(22) Filed: Jul. 21, 2023

(65) Prior Publication Data

US 2024/0025859 A1  Jan. 25, 2024

Related U.S. Application Data

(63) Continuation of application No. 17/621,827, filed as application No. PCT/IB2020/055994 on Jun. 24, 2020, now Pat. No. 11,753,382.

(60) Provisional application No. 62/866,321, filed on Jun. 25, 2019.

(51) Int. Cl.
 *C07D 231/56* (2006.01)
(52) U.S. Cl.
 CPC .................. *C07D 231/56* (2013.01)
(58) Field of Classification Search
 CPC .................................................. C07D 231/56
 See application file for complete search history.

(56) References Cited

U.S. PATENT DOCUMENTS

| | | | |
|---|---|---|---|
| 4,451,477 A | 5/1984 | Silvestrini et al. |
| 4,999,367 A | 3/1991 | Baiocchi et al. |
| 5,112,986 A | 5/1992 | Baiocchi et al. |
| 5,278,183 A | 1/1994 | Silvestrini |
| 6,020,356 A | 2/2000 | Guglielmotti et al. |
| 6,093,743 A | 7/2000 | Lai et al. |
| 6,274,627 B1 | 8/2001 | Lai et al. |
| 6,316,502 B1 | 11/2001 | Lai et al. |
| 6,319,517 B1 | 11/2001 | Cavallo et al. |
| 6,337,087 B1 | 1/2002 | Cavallo et al. |
| 6,534,534 B1 | 3/2003 | Guglielmotti et al. |
| 6,589,991 B1 | 7/2003 | Lai et al. |
| 6,596,770 B2 | 7/2003 | Lai et al. |
| 6,649,591 B2 | 11/2003 | Lai |
| 6,673,908 B1 | 1/2004 | Stanton, Jr. |
| 6,818,629 B2 | 11/2004 | Peterson et al. |
| 7,553,496 B2 | 6/2009 | Ambati |
| 7,732,162 B2 | 6/2010 | Hoffman et al. |
| 7,816,497 B2 | 10/2010 | Ambati |
| 7,919,518 B2 | 4/2011 | Guglielmotti et al. |
| 7,928,284 B2 | 4/2011 | Ambati |
| 8,008,092 B2 | 8/2011 | Ambati |
| 8,067,031 B2 | 11/2011 | Daniloff et al. |
| 8,158,152 B2 | 4/2012 | Palepu |
| 8,198,310 B2 | 6/2012 | Guglielmotti et al. |
| 8,232,265 B2 | 7/2012 | Rogers et al. |
| 8,314,099 B2 | 11/2012 | Guglielmotti et al. |
| 8,350,052 B2 * | 1/2013 | Caracciolo Torchiarolo ............... C07D 231/56 548/362.5 |
| 8,354,544 B2 * | 1/2013 | Caracciolo Torchiarolo ............... C07D 231/56 548/362.5 |
| 8,461,194 B2 | 6/2013 | Guglielmotti |
| 8,835,481 B2 | 6/2014 | Guglielmotti et al. |
| 8,999,292 B2 | 4/2015 | Boyd |
| 9,370,484 B2 | 6/2016 | Boyd |
| 9,662,407 B2 | 5/2017 | Boyd |
| 9,820,969 B2 | 11/2017 | Boyd |
| 9,999,688 B2 | 6/2018 | Boyd |
| 10,265,418 B2 | 4/2019 | Boyd |
| 10,420,848 B2 | 9/2019 | Boyd |
| 10,537,647 B2 | 1/2020 | Boyd |
| 10,646,592 B2 | 5/2020 | Boyd |
| 11,110,184 B2 | 9/2021 | Boyd |
| 11,753,382 B2 * | 9/2023 | Jiao ....................... C07D 231/56 548/360.1 |
| 2003/0207309 A1 | 11/2003 | Hageman et al. |
| 2004/0177387 A1 | 9/2004 | Jayakrishna |

(Continued)

FOREIGN PATENT DOCUMENTS

| | | |
|---|---|---|
| CA | 2860382 A1 | 6/2013 |
| CA | 2911041 A1 | 11/2013 |

(Continued)

OTHER PUBLICATIONS

Ambati, et al., "An animal model of age-related macular degeneration in senescent Col-2 or Cor2-deficient mice," Nature Medicine, vol. 9, No. 11, pp. 1390-1397, Nov. 2003.
Arnold, et al., "Reticular Pseudodrusen. A Risk Factor in Age-Related Maculopathy," Retina, vol. 15, No. 3, pp. 183-191, 1995.
Beckmann, et al., "In vivo visualization of macrophage infiltration and activity in inflammation using magnetic resonance imaging," WIRES Nanomedicine and Nanbiotechnology, vol. 1, 272-298, 2009.
Bindewald, et al., "Classification of abnormal fundus autofluorescence patterns in the junctional zone of geographic atrophy in patients with age related macular degeneration," Br J Ophthalmol., vol. 89, pp. 874-878, 2005.
Bindewald, et al., "Classification of Fundus Autofluorescence Patterns in Early Age-Related Macular Disease," IOVS, vol. 46, No. 9, pp. 3309-3314, 2005.

(Continued)

*Primary Examiner* — D Margaret M Seaman
(74) *Attorney, Agent, or Firm* — Morgan, Lewis & Bockius LLP

(57) ABSTRACT

The invention in this disclosure is related to the processes of making Bindarit or derivatives thereof. Specifically, the present invention provides, in part, new processes for making 2-((1-benzyl-1H-indazol-3-yl)methoxy)-2-methylpropanoic acid and its derivatives. By way of non-limiting example, synthesis and purification processes of 2-((1-benzyl-1H-indazol-3-yl)methoxy)-2-methylpropanoic acid are provided by the invention in this disclosure.

9 Claims, No Drawings

(56) References Cited

U.S. PATENT DOCUMENTS

| | | |
|---|---|---|
| 2006/0067935 A1 | 3/2006 | Ambati |
| 2006/0135423 A1 | 6/2006 | Ambati |
| 2006/0263409 A1 | 11/2006 | Peyman |
| 2007/0015771 A1 | 1/2007 | Matteucci et al. |
| 2007/0043057 A1 | 2/2007 | Matteucci et al. |
| 2007/0059336 A1 | 3/2007 | Hughes et al. |
| 2007/0190055 A1 | 8/2007 | Ambati |
| 2007/0191273 A1 | 8/2007 | Ambati et al. |
| 2008/0299130 A1 | 12/2008 | Ambati |
| 2009/0123375 A1 | 5/2009 | Ambati |
| 2009/0155176 A1 | 6/2009 | Burnier et al. |
| 2009/0186376 A1 | 7/2009 | Ambati et al. |
| 2009/0260091 A1 | 10/2009 | Ambati |
| 2010/0317618 A1 | 12/2010 | Guglielmotti et al. |
| 2011/0097390 A1 | 4/2011 | Ambati |
| 2011/0182908 A1 | 7/2011 | Hageman et al. |
| 2011/0268723 A1 | 11/2011 | Ambati |
| 2012/0064010 A1 | 3/2012 | Ambati et al. |
| 2015/0044205 A1 | 2/2015 | Yaspan et al. |

FOREIGN PATENT DOCUMENTS

| | | |
|---|---|---|
| CA | 2870353 41 | 5/2016 |
| EP | 0131317 81 | 1/1985 |
| EP | 0382276 B1 | 8/1995 |
| WO | WO 98/36736 A1 | 8/1988 |
| WO | WO 97/16185 A2 | 5/1997 |
| WO | WO 98/36735 A1 | 8/1998 |
| WO | WO 2004/041160 A2 | 5/2004 |
| WO | WO 2005/108431 A1 | 11/2005 |
| WO | WO 2007/098113 A2 | 8/2007 |
| WO | WO 2007/133800 A2 | 11/2007 |
| WO | WO 2008/061671 A2 | 5/2008 |
| WO | WO 2009/105260 A2 | 8/2009 |
| WO | WO 2009/109613 A2 | 9/2009 |
| WO | WO 2009/109616 A2 | 9/2009 |
| WO | WO 2009/109618 A2 | 9/2009 |
| WO | WO 2009/109684 A2 | 9/2009 |
| WO | WO 2010/129843 A1 | 11/2010 |
| WO | WO 2010/138591 A1 | 12/2010 |
| WO | WO 2011/015501 A1 | 2/2011 |
| WO | WO 2011/015502 A1 | 2/2011 |
| WO | WO 2011/036047 A1 | 3/2011 |
| WO | WO 2011/085007 A1 | 7/2011 |
| WO | WO 2011/153234 A2 | 12/2011 |
| WO | WO 2013/037960 A1 | 3/2013 |
| WO | WO 2013/163758 A1 | 11/2013 |
| WO | WO 2015/173786 A1 | 11/2015 |

OTHER PUBLICATIONS

Boretsky, et al., "Quantitative Evaluation of Retinal Response to Laser Photocoagulation Using Dual-Wavelength Fundus Autofluorescence Imaging in a Small Animal Nodel," IOVS, vol. 52, No. 9, pp. 6300-6307, 2011.
Boyd, et al., "Reticular Fundus Autofluorescence (FAF) In The Evolution of Geographic Atrophy (GA) In A Rat Model of RPE Toxicity," 2012 ARVO Annual Meeting, Abstract of Program#Poster#6504/A430, 2 pages, May 10, 2012.
Buono, et al., "Fluorescent pegylated nanoparticles demostrate fluid-phase pinocytosis by macrophages in mouse atheroscienotic lesions," J Clin. Invest, vol. 119, No. 5, pp. 1373-1381, 2009.
Chen, et al., "Effects of quercetin on the expressin of MCP-1, MMO-9 and VEGF in rates with diabetic retinopathy," Experimental And Therapeutic Medicine, vol. 14, pp. 6022-6062, 2017.
Chiu, et al., "Modulation of morphological changes in microglia and neuroprotection by moncyte chemoattractant protein-1 in experimental glaucoma," Cellular & Molecular Immunology, vol. 7, pp. 61-68, 2010.
Cone, et al., "Regulation Of Experimental Autoimmune Uveitis (EAU) Induction In Mice By The Phosphodiesterase Inhibitor Dipyrimidol And Of Active EAU By Bindrit, An Inhibitor Of Monocyte Chemotactic Proteins," 2011 ARVO Annual Meeting, Abstract of Program#Poster#2260/A426, 5 pages, May 2, 2011.
Definition of "treat" from Cambridge English Dictionary, https://dictionary.cambridge.org/dictionary/english/treatment/dataset-cacd, accessed Jan. 2, 2019.
Dong, et al., "Upregulation of Retinal Neuronal MCP-1 in the Rodent Model of Diabetic Retinopaty and Its Function In Vitro," IOVS, vol. 53, No. 12, pp. 7567-7575, 2012.
Duker, "The COMPLETE Trial for AMD: Results," Review of Ophthalmolgy, Sep. 6, 2012, 3 pages.
Enzmann, et al., "Behavioral and anatomical abnormalities in a sodium iodate-induced model of retinal pigment epithelium degeneration," Exp Eye Res., vol. 82, pp. 441-448, 2006.
Eter, et al., "In Vivo Visualization of the Dendritic Cells, Macrophages, And Microglial Cells Responding to Laser-Induced Damage in the Fundus of the Eye," Invest. Ophthalmol Vis. Sci., vol. 49, No. 8, pp. 3649-3568, 2008.
Fleckenstein, et al., "Fundus Autofluorescence and Spectral-Domain Optical Coherence Tomography Characteristics in a Rapidly Progressing Form of Geographic Atrophy," Invest. Ophthalmol. Vis. Sci., vol. 52, No. 6, pp. 3761-3766, 2011.
Fleckenstein, et al., "High-Resolution Spectral Domain-OCT Imaging in Geographic Atrophy Associated with Age-Related Macular Degeneration," IOVS, vol. 49, No. 9, pp. 4137-4144, Sep. 2003.
Franco, et al., "Decreased Visual Function after Patchy Loss of Retinal Pigment Epithelium Induced by Low-Dose Sodium Iodate," IOVS, vol. 50, No. 8, pp. 4004-4010, 2009.
Gale, et al., "A CCR2/5 Inhibitor, PF-04634817, is Inferior to Monthly Ranibizumab in the Treatment of Diabetic Macular Edema," Investigative Ophthalmology & Visual Science, vol. 59, 6, pp. 2659-2669, May 2018.
Gazzaniga, et al., "Target Tumor-Associated Macrophages and Inhibition of MCP-1 Reduce Angiogenesis and Tumor Growth in a Human Melanoma Xenograft," Journal of Investigative Dermatology, vol. 127, No. 8, pp. 2031-2041, 2007.
Hua, et al., "In vivo imaging of choroidal angiogenesis using fluorescence-labeled cationic liposomes," Molecular Vision, vol. 18, pp. 1045-1054, 2012.
International Search Report & Written Opinion, PCT Application No. PCT/CA2013/050335, dated Aug. 23, 2013, 12 pages.
International Search Report & Written Opinion, PCT Application No. PCT/IB2015/053609, dated Sep. 1, 2015, 15 pages.
International Search Report & Written Opinion, PCT Application No. PCT/IB2016/000958, dated Sep. 30, 2016, 18 pages.
Kalinowska, et al., "Investigational C—C chemokine receptor 2 antagonists for the treatment of autoimmune diseases," Expert Opin Invest, Drugs, vol. 17, No. 9, pp. 1267-1279, 2008.
Kiuchi, et al., "Morphologic characteristics of retinal degneration induced by sodium iodate in mice," Curr Ey Res., vol. 25, No. 6, pp. 373-379, 2002.
Ladewig, et al., "Prostaglandin $E_1$ infusion therapy in dry age-related macular degeneration," Prostaglandins, Leukotriones, and Essental Fatty Acids, vol. 72, pp. 251-256, 2005.
Lois, et al., "Fundus Autofluoresecne in Patients With Age-related Macular Degeneration and High Risk of Visual Loss," Am. J. Opthalmol., vol. 133, pp. 341-349, 2002.
Luhmann, et al., "The Drusenliek Phenotype in Aging Col2-Knockout Mice is Caused by an Accelerated Accumulation of Swollen Autofluorsecent Subretinal Macrophages." Invest. Ophthalmol Vis. Sci., vol. 50, pp. 5934-5943, 2009.
Mendes Jorge, et al., "Scavenger Function of Resident Autofluorescent Perivascular Macrophages and Their Contribution to the Maintenance of the Blood-Retinal Barrier." Invest. Ophthalmol. Vis. Sci., vol. 50, No. 12, pp. 5997-6005, 2009.
Mizota, et al., "Functional Recovery of Retina After Sodium Iodate Infection in Mice," Vision Res., vol. 37, No. 14, pp. 1859-1865, 1997.
Mori et al. "The Ultra-Late Phase of Indocyanine Green Angiography for Healthy Subjects And Patients With Age-Related Macular Degeneration," Retina, vol. 22, pp. 309-316, 2002.
Narasaraju, et al., "MCP-1 Antibody Treatment Enhances Damage and Impedes Repair of the Alvedar Epithelium in Influenza Pneumontis," Am. J. Respir. Cell Mol. Biol., vol. 42, pp. 732-743, 2010.

(56) References Cited

OTHER PUBLICATIONS

Novack, "Pharmacotherapy for the Treament of Choroidal Neovascularization Due to Age-Related Macular Degneration," Annual Review of Pharmacology and Toxicology, vol. 48, No. 1, pp. 61-78, 2008.
Obata, et al., "Retinal degeneration is delayed by tissue factor pathway inhibitor-2 in RCS rats and a sodium-iodate-induced model in rabbits," Eye, vol. 19, pp. 464-468, 2005.
Ohtaka, et al., "Protective Effect of Hepatocyte Growth Factor Against Degeneration of the Retinal Pigment Epithelium and Photoreceptor in Sodium Iodate-Injected Rats," Curr. Eye Res., vol. 31, pp. 347-355, 2006.
Peterman, "The 4 Stages of Diabetic Retinopathy: What You Can Expect," https://www.griswoldhomecare.com/blog/2015/january/the-4-stages-of-diabetic-retinopathy-what-ca/, Jan. 15, 2015.
Raoul, et al., "CCL2/CCR2 and CX3CL1/CX3CR1 chemokine axes and their possible involvement in age-related macular degeneration," Journal of Neuroinflammation, vol. 7, No. 87, 7 pages, 2010.
Rodrigues, et al., "The Use of Vital Dyes in Ocular Surgery," Servey of Ophthalmology, vol. 54, No. 5, pp. 576-617, 2009.
Ross, et al., "Immunological protein expression profile Ccl2/Cx3cr1 deficient mice with lesions similar to age-related macular degeneration," Exp Eye Res., vol. 86, No. 4, pp. 675-683, Apr. 2008.
Sarks, et al., "Evolution of reticular pseudodrusen," Br. J. Ophthalmol. vol. 95, pp. 979-985, 2011.
Spencer, et al., "In vivo imaging of the immune response in the eye," Semin. Immunopathol., vol. 30, pp. 179-190, 2008.
Tanaka, et al., "Third-Order Neuronal Responses Contribute to Shaping the Negative Electroretinogram in Sodium Iodate-Treated Rats," Curr. Eye Res. vol. 30, pp. 443-453, 2005.
Tesch, et al., "Monocyte Chemoattractant Protein 1-dependant Leukocytic Infiltrates Are Responsible for Autoimmune Disease in MRL•Fas$^{lpr}$ Mice," J. Exp. Med., vol. 190, No. 12, pp. 1813-1824, 1999.
Wolf, et al., "Targeting the pro-inflammatory factor CCL2 (MCP-1) with Bindant for influenza A (H7N9) treatment," Clinical & Translational Immunology, vol. 6, 13 pages, 2017.
Wroblewski, et al., "Indocyanine Green Angiography in Stargardt's Flavimaculatus," Am. J Opthalmolgy, vol. 120, pp. 208-2018, 1995.
Yoshioka, et al., "Monocyte chemoattractant protein-1-2518 polymorphism is not associated with diabetic retinopathy in Japanese type 2 diabetes," Diabetes & Metabolic Syndrome: Clinical Research & Reviews, vol. 3, pp. 166-168, 2009.
Zeng, et al., "Labelling of retinal microglial cells following an intravenous injection of fluorsecent dye into rates of different ages," J. Anat., vol. 196, pp. 173-179, 2000.
Zhao, et al., "Patches of RPE Loss Can Be Detected In Vivo In The Rat Eye Using Confocal Scanning Laser Ophthalmoscopy," 2011 ARVO Annual Meeting, Abstract of Program#Poster#969/A161, 2 pages, May 1, 2011.
Zweifel, et al., "Prevalence and Significance of Subretinal Drusenoid Deposits (Reticular Pseudodrusen) in Age-Related Macular Degeneration," Ophthalmology, vol. 117, No. 9, pp. 1775-1781, 2010.
Zweifel, et al., "Reticular Pseudodrusen Are Subretinal Drusenoid Deposits," Ophthalmology, vol. 117, No. 2, pp. 303-312, 2010.
International Search Report & Written Opinion PCT Application No. PCT/IB2020/055994, dated Nov. 18, 2020, 12 pages.

* cited by examiner

PROCESSES OF MAKING 2-((1-BENZYL-1H-INDAZOL-3-YL)METHOXY)-2-METHYLPROPANOIC ACID AND ITS DERIVATIVES

CROSS-REFERENCE TO RELATED APPLICATIONS

This application claims the benefit of U.S. Provisional Application No. 62/866,321, filed Jun. 25, 2019, the entire contents of which are hereby incorporated by reference in their entirety.

FIELD OF THE INVENTION

The present invention provides new processes for making 2-((1-benzyl-1H-indazol-3-yl)methoxy)-2-methylpropanoic acid and its derivatives.

BACKGROUND OF THE INVENTION

Bindarit (2-((1-benzyl-1H-indazol-3-yl)methoxy)-2-methylpropanoic acid) is an effective anti-inflammatory small molecule. Recently, bindarit has been shown to be an effective agent for the treatment of various blinding eye diseases (see WO 2013/163758 and WO 2015/173786).

Various processes for the preparation of Bindarit have been described in EP 0382276 and WO 2011015502. However, the processes described therein normally involve harsh reaction conditions, less stable starting reagents, and have relatively low yield.

There exists a need for a reliable and scalable process of making Bindarit or its derivatives thereof under mild, and safer conditions. The present invention meets such need.

SUMMARY OF THE INVENTION

In one aspect, the present disclosure provides a process of making the compound of Formula (I)

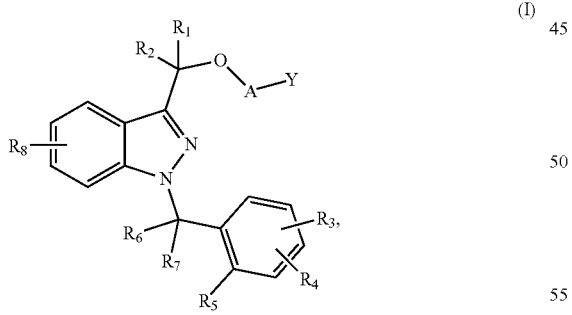

the process comprising: reacting the compound of Formula (II)

in the presence of $(R_{16})_4NZ$ with the compound of Formula (III)

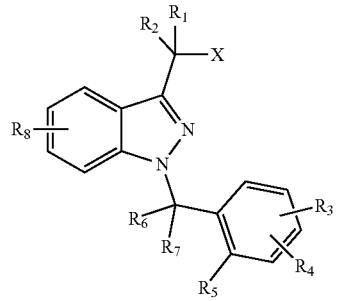

to form the compound of Formula (I);

wherein: A may be a bond σ, —$X_1$—, or —$X_1$—O—$X_2$—, in which $X_1$ and $X_2$, which may be identical or different from each other, may be an alkyl group having from 1 to 5 carbon atoms, optionally substituted with one or more alkyl groups having from 1 to 5 carbon atoms or one or more alkoxy groups having from 1 to 3 carbon atoms, Y is H when A is a bond σ, or Y may be H, —OH, or —N($R_{11}$)($R_{12}$), when A is —$X_1$— or —$X_1$—O—$X_2$—, in which $R_{11}$ may be hydrogen, an alkyl group having from 1 to 5 carbon atoms, or $R_{11}$ together with $R_{12}$ forms a 4- to 7-membered heterocycle, $R_{12}$ may be hydrogen, an alkyl group having from 1 to 5 carbon atoms, or $R_{12}$ together with $R_{11}$ forms a 4- to 7-membered heterocycle, $R_1$ and $R_2$, which may be identical or different from each other, may be hydrogen, an alkyl group having from 1 to 5 carbon atoms, $R_3$, $R_4$ and $R_8$, which may be identical or different from each other, may be hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —$SO_2$NR'R", —$SO_2$R', nitro and trifluoromethyl; with R' and R", which may be identical or different from each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, —OH, —N(R)(R"), —N(R')COR", nitro and trifluoromethyl, or $R_5$ together with one from between $R_6$ and $R_7$ forms a ring having 5 or 6 carbon atoms; with R' and R", which may be identical or different from each other, represented by hydrogen and an alkyl group having from 1 to 5 carbon atoms, $R_6$ and $R_7$, which may be identical or different from each other, may be hydrogen, an alkyl group having from 1 to 5 carbon atoms, or together form a group C=O, or one from between $R_6$ and $R_7$, together with $R_5$, forms a ring having 5 or 6 carbon atoms, $R_{16}$ is an alkyl group having from 1 to 5 carbon atoms, X is a leaving group, Z is I, Br, or Cl.

In another aspect, the present disclosure provides a process of making the compound of Formula (XIII)

(XIII)

[Structure of Formula (XIII): indazole with R8 substituent, R1/R2 groups with O-A-C(=O)-Y, and N-substituted with R6/R7/C-aryl bearing R3, R4, R5]

the process comprising: reacting the compound of Formula (XIV)

(XIV)

$$HO-A-C(=O)-Y_1$$

in the presence of $(R_{16})_4NZ$ with the compound of Formula (III)

(III)

[Structure of Formula (III): indazole with R8, R1/R2-X, and N-substituted aryl with R3, R4, R5, R6, R7]

to form the compound of Formula (XIII); wherein:

A may be $-X_1$ or $-X_1-OC(R_9)(R_{10})-$, in which
  $X_1$ may be an alkyl group having from 1 to 5 carbon atoms, optionally substituted with one or more alkyl groups having from 1 to 5 carbon atoms or one or more alkoxy groups having from 1 to 3 carbon atoms, and
  $R_9$ and $R_{10}$, which may be identical or different from each other, may be hydrogen, an alkyl group having from 1 to 5 carbon atoms or an alkoxy group having from 1 to 3 carbon atoms, Y, $Y_1$ each independently is $-OR_{13}$, $N(R_{11})(R_{12})$, $N(R_{13})O(R_{14})$, $N(R_{13})N(R_{14})(R_{15})$, $N(R_{13})-X_2-N(R_{14})(R_{15})$, or $N(R_{13})-X_2-CO-X_3$, in which
  $R_{11}$ may be hydrogen, an alkyl group having from 1 to 5 carbon atoms, an alkoxy group having from 1 to 3 carbon atoms, or $R_{11}$ together with $R_{12}$ forms a 4- to 7-membered heterocycle,
  $R_{12}$ may be hydrogen, an alkyl group having from 1 to 5 carbon atoms, an alkoxy group having from 1 to 3 carbon atoms, an aryl group, a heteroaryl group, an alkylaryl group, an alkylheteroaryl group, COR', COOR', CON(R')(R") with R' and R", which may be identical or different from each other, represented by hydrogen and an alkyl group having from 1 to 5 carbon atoms, or $R_{12}$ together with $R_{11}$, forms a 4- to 7-membered heterocycle, $R_{13}$ and $R_{15}$, which may be identical or different from each other, may be hydrogen, an alkyl group having from 1 to 5 carbon atoms or an alkoxy group having from 1 to 3 carbon atoms, $R_{14}$ may be hydrogen, an alkyl group having from 1 to 5 carbon atoms, an aryl group, a heteroaryl group, an alkylaryl group, an alkylheteroaryl group, COR', COOR', CON(R')(R") with R' and R", which may be identical or different from each other, represented by hydrogen and an alkyl group having from 1 to 5 carbon atoms, $X_2$ may be an alkyl group having from 1 to 5 carbon atoms, optionally substituted with one or more alkyl groups having from 1 to 5 carbon atoms or one or more alkoxy groups having from 1 to 3 carbon atoms, $X_3$ may be OH, $NH_2$, NHOH or $NHNH_2$, $R_1$ and $R_2$, which may be identical or different from each other, may be hydrogen, an alkyl group having from 1 to 5 carbon atoms or an alkoxy group having from 1 to 3 carbon atoms, $R_3$, $R_4$ and $R_8$, which may be identical or different from each other, may be hydrogen, an alkyl group having from 1 to 5 carbon atoms, an alkoxy group having from 1 to 3 carbon atoms, a halogen atom, $-OH$, $-N(R')(R")$, $-N(R')COR"$, $-CN$, $-CONR'R"$, $-SO_2NR'R"$, $-SO_2R'$, nitro and trifluoromethyl; with R' and R", which may be identical or different from each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, $-OH$, $-N(R')(R")$, $-N(R')COR"$, nitro and trifluoromethyl, or $R_5$ together with one from among $R_6$ and $R_7$ forms a ring having 5 or 6 carbon atoms; with R' and R", which may be identical or different from each other, represented by hydrogen and an alkyl group having from 1 to 5 carbon atoms, $R_6$ and $R_7$, which may be identical or different from each other, may be hydrogen, an alkyl group having from 1 to 5 carbon atoms, or together form a group C=O, or one from among $R_6$ and $R_7$, together with $R_5$, forms a ring having 5 or 6 carbon atoms, $R_{16}$ is an alkyl group having from 1 to 5 carbon atoms, X is a leaving group, Z is I, Br, or Cl.

In another aspect, the present invention provides of a process of making the compound of Formula (IV)

(IV)

[Structure of Formula (IV): indazole with CH2-O-C(CH3)2-COOH at 3-position and N-CH2-Ph]

the process comprising: reacting the compound of Formula (V)

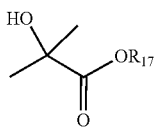

in the presence of $(R_{16})_4NZ$ with the compound of Formula (VI)

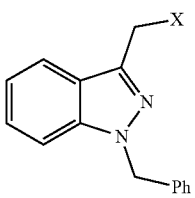

to form the compound of Formula (IV); wherein: $R_{16}$, $R_{17}$ each independently is an alkyl group having from 1 to 5 carbon atoms, X is a leaving group, Z is I, Br, or Cl.

DETAILED DESCRIPTION OF THE INVENTION

This disclosure describes a new process for the synthesis of 2-((1-benzyl-1H-indazol-3-yl)methoxy)-2-methylpropanoic acid and derivatives thereof.

In an embodiment, this disclosure describes a new process for making 2-((1-benzyl-1H-indazol-3-yl)methoxy)-2-methylpropanoic acid (Formula (IV)) from deprotonation of ethyl 2-hydroxy-2-methylpropionate and then reaction with 1-benzyl-3-chloromethyl-1H-indazole. The resulting intermediate, ethyl 2-((1-benzyl-1H-indazol-3-yl)methoxy)-2-methylpropanoate is a liquid and is hydrolyzed without isolation to form the final product 2-((1-benzyl-1H-indazol-3-yl)methoxy)-2-methylpropanoic acid (Formula (IV)).

Different processes of making 2-((1-benzyl-1H-indazol-3-yl)methoxy)-2-methylpropanoic acid have been described in EP 0382276 and WO 2011/015502. However, the processes of synthesis known in the art and described therein have a number of disadvantages.

Firstly, the intermediate 1-benzyl-1 (H)-indazol-3-carboxylic acid is expensive obtain and cannot be easily obtained on the market.

Second, the reaction route, described in EP 0382276, provides for the use of thionyl chloride to convert the 1-benzyl-3-hydroxymethyl-1H-indazole into the corresponding 3-chloromethyl derivative. The use of thionyl chloride, a highly toxic substance, gives rise to considerable safety and management problems in industrial processes.

Third, the Bargellini reaction, described in EP 0382276, has shown industrial disadvantages in low yields (less than 50%), the production of carbon monoxide, a toxic and flammable gas, and the generation of significant exothermic phenomena which are difficult to manage industrially.

Fourth, the Grignard reaction route, described in WO 2011/015502, is difficult for industrial application due to its harsh condition, poor stability, and generation of excess impurity.

The present invention provides a new process making 2-((1-benzyl-1H-indazol-3-yl)methoxy)-2-methylpropanoic acid and derivatives thereof. The new process is scalable, safe, reliable and reproducible.

Definitions

As used in the preceding sections and throughout the rest of this specification, unless defined otherwise, all the technical and scientific terms used herein have the same meaning as is commonly understood by one of skill in the art to which this invention belongs. All patents and publications referred to herein are incorporated by reference in their entireties.

The terms "a," "an," and "the" as used herein, generally are construed to cover both the singular and the plural forms.

As used, herein the term "alkyl" refers to a straight or branched hydrocarbon chain radical including monovalent radical and divalent radical consisting solely of carbon and hydrogen atoms, containing no unsaturation, having from one to ten carbon atoms (e.g., (C1-10)alkyl or C1-10 alkyl). Whenever it appears herein, a numerical range such as "1 to 10" refers to each integer in the given range—e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Examples of "alkyl" as used herein include, but are not limited to, methyl, ethyl, propyl, isopropyl, isobutyl, n-butyl, tert-butyl, isopentyl, and n-pentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —ORa, —SRa, —N(Ra)$_2$, where each Ra is independently hydrogen, fluoroalkyl, carbocyclyl, carbocyclylalkyl, aryl, aralkyl, heterocycloalkyl, heterocycloalkylalkyl, heteroaryl or heteroarylalkyl.

The terms "substituted" or "optionally substituted" refer to chemical moieties, wherein one or more hydrogen atoms may be replaced by a halogen atom, —SH, NO2 or —OH group, or by an alkyl, alkenyl, alkanoyl, heteroalkyl, aryl, heteroaryl, cycloalkyl or heterocycle group as defined herein. The last-mentioned groups may be optionally substituted.

Abbreviation

DBU=1,8-Diazabicyclo[5.4.0]undec-7-ene

IPEA=N,N-Diisopropylethylamine

DMF=N,N-Dimethylformamide

THF=Tetrahydrofuran

EtOAc=Ethyl acetate

UPLC=Ultra-Performance Liquid Chromatography

MTBE=Methyl tert-butyl ether

ACN=Acetonitrile

In one aspect, the present disclosure provides a process of making the compound of Formula (I)

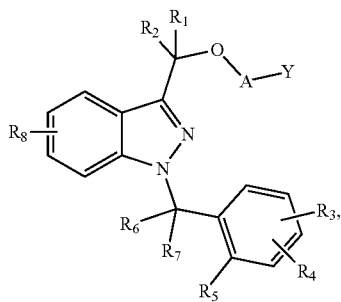

the process comprising: reacting the compound of Formula (II)

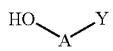

in the presence of $(R_{16})_4NZ$ with the compound of Formula (III)

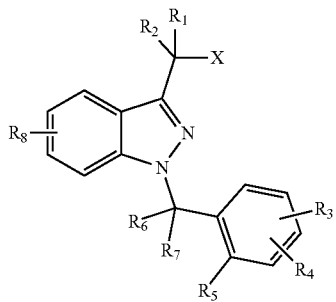

to form the compound of Formula (I);
wherein: A may be a bond σ, —$X_1$—, —$X_1$—O—$X_2$—, in which
$X_1$ and $X_2$, which may be identical or different from each other, may be an alkyl group having from 1 to 5 carbon atoms, optionally substituted with one or more alkyl groups having from 1 to 5 carbon atoms or one or more alkoxy groups having from 1 to 3 carbon atoms,
Y is H when A is a bond σ, or Y may be H, —OH, or —N($R_{11}$)($R_{12}$), when A is —$X_1$— or —$X_1$—O—$X_2$—, in which
$R_{11}$ may be hydrogen, an alkyl group having from 1 to 5 carbon atoms, or $R_{11}$ together with $R_{12}$ forms a 4- to 7-membered heterocycle,
$R_{12}$ may be hydrogen, an alkyl group having from 1 to 5 carbon atoms, or $R_{12}$ together with $R_{11}$ forms a 4- to 7-membered heterocycle,
$R_1$ and $R_2$, which may be identical or different from each other, may be hydrogen, an alkyl group having from 1 to 5 carbon atoms,
$R_3$, $R_4$ and $R_8$, which may be identical or different from each other, may be hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —$SO_2NR'R"$, —$SO_2R'$, nitro and trifluoromethyl;

with R' and R", which may be identical or different from each other, represented by hydrogen and an alkyl group having from 1 to 5 carbon atoms,
$R_5$ may be hydrogen, an alkyl group having from 1 to 5 carbon atoms, an alkoxy group having from 1 to 3 carbon atoms, a halogen atom, —OH, —N(R)(R"), —N(R')COR", nitro and trifluoromethyl, or $R_5$ together with one from between $R_6$ and $R_7$ forms a ring having 5 or 6 carbon atoms; with R' and R", which may be identical or different from each other, represented by hydrogen and an alkyl group having from 1 to 5 carbon atoms,
$R_6$ and $R_7$, which may be identical or different from each other, may be hydrogen, an alkyl group having from 1 to 5 carbon atoms, or together form a group C=O, or one from between $R_6$ and $R_7$, together with $R_5$, forms a ring having 5 or 6 carbon atoms,
$R_{16}$ is an alkyl group having from 1 to 5 carbon atoms,
X is a leaving group,
Z is I, Br, or Cl.

In an embodiment, X is Br or Cl.
In certain embodiments, the compounds can be made via the process described herein are the compounds of Formula (I) wherein: if $R_8$ is a hydrogen atom, then the group linked to the nitrogen atom in the 1-position of the indazole ring is different from a benzyl group, a 4-chlorobenzyl group, or a 2-4-dichlorobenzyl group; if $R_8$ is a fluorine atom in the 5-position of the indazole ring, then the group linked to the nitrogen atom in the 1-position of the indazole ring is different from 5-chloro-2-methoxybenzyl group; and if $R_8$ is a trifluoromethyl group in the 6-position of the indazole ring, then the group linked to the nitrogen atom in the 1-position of the indazole ring is different from a 2-4-dichlorobenzyl group.

In some embodiments, the compound of Formula (I) is selected from:
1-benzyl-3-hydroxymethyl-indazole;
1-(4-methoxybenzyl)-1H-indazol-3-yl]methanol;
1-(4-methylbenzyl)-1H-indazol-3-yl]methanol;
1-(4-chlorobenzyl)-1H-indazol-3-yl]methanol;
1-(3,4-dichlorobenzyl)-1H-indazol-3-yl]methanol;
1-(2,4-dichlorobenzyl)-1H-indazol-3-yl]methanol;
1-(4-fluorobenzyl)-1H-indazol-3-yl]methanol;
1-(4-chloro-2-methylbenzyl)-1H-indazol-3-yl]methanol;
1-benzyl-5-methoxy-1H-indazol-3-yl)methanol;
1-benzyl-5-methoxy-1H-indazole-3-carboxylate;
2-[1-(4-chloro-2-methylbenzyl)-1H-indazol-3-yl]propan-2-ol;
1-(4-chloro-2-methylbenzyl)-1H-indazole-3-carboxylate;
2-[1-(2,4-dichlorobenzyl)-1H-indazol-3-yl]propan-2-ol;
1-(2,4-dichlorobenzyl)-1H-indazole-3-carboxylate;
1-[1-(4-chloro-2-methylbenzyl)-1H-indazol-3-yl]ethanol;
1-(4-chloro-2-methylbenzyl)-1H-indazole-3-carboxaldehyde;
1-[1-(4-chloro-2-methylbenzyl)-1H-indazol-3-yl]ethanol
1-(4-chloro-2-methylbenzyl)-1H-indazole-3-carboxaldehyde;
2-[(1-benzyl-1H-indazol-3-yl)methoxy]ethanol;
2-[(1-benzyl-1H-indazol-3-yl)methoxy]-N,N-dimethylethanamine hydrochloride;
3-[(1-benzyl-1H-indazol-3-yl)methoxy]-N,N-dimethylpropan-1-amine hydrochloride;
3-[(1-benzyl-1H-indazol-3-yl)methoxy]propan-1-ol;
2-[(1-benzyl-1H-indazol-3-yl)methoxy]-2-methylpropan-1-ol;
1-benzyl-3-[(1,1-dimethyl-2-morpholin-4-ylethoxy) methyl]-1H-indazole maleate; and 1-benzyl-3-[(1,1-dimethyl-2-morpholin-4-yl-2-oxyethoxy) methyl]-1H-indazole.

In another aspect, the present disclosure provides a process of making the compound of Formula (XIII)

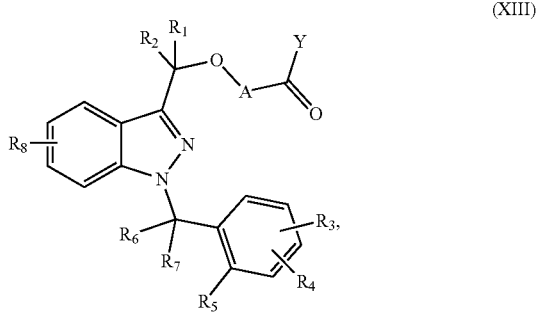

(XIII)

the process comprising: reacting the compound of Formula (XIV)

(XIV)

in the presence of $(R_{16})_4NZ$ with the compound of Formula (III)

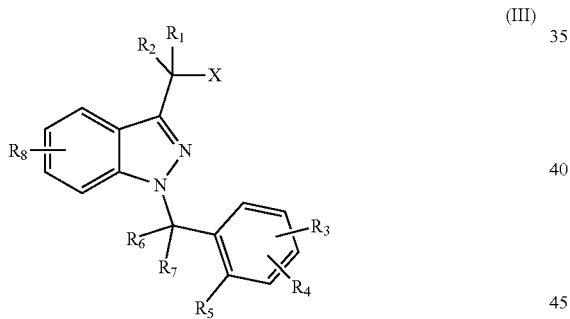

(III)

to form the compound of Formula (XIII); wherein:

A may be —$X_1$ or —$X_1$—$OC(R_9)(R_{10})$—, in which
  $X_1$ may be an alkyl group having from 1 to 5 carbon atoms, optionally substituted with one or more alkyl groups having from 1 to 5 carbon atoms or one or more alkoxy groups having from 1 to 3 carbon atoms, and
  $R_9$ and $R_{10}$, which may be identical or different from each other, may be hydrogen, an alkyl group having from 1 to 5 carbon atoms or an alkoxy group having from 1 to 3 carbon atoms, Y, $Y_1$ each independently is —$OR_{13}$, $N(R_{11})(R_{12})$, $N(R_{13})O(R_{14})$, $N(R_{13})N(R_{14})(R_{15})$, $N(R_{13})$—$X_2$—$N(R_{14})(R_{15})$, or $N(R_{13})$—$X_2$—CO—$X_3$, in which
  $R_{11}$ may be hydrogen, an alkyl group having from 1 to 5 carbon atoms, an alkoxy group having from 1 to 3 carbon atoms, or $R_{11}$ together with $R_{12}$ forms a 4- to 7-membered heterocycle,
  $R_{12}$ may be hydrogen, an alkyl group having from 1 to 5 carbon atoms, an alkoxy group having from 1 to 3 carbon atoms, an aryl group, a heteroaryl group, an alkylaryl group, an alkylheteroaryl group, COR', COOR', CON(R')(R") with R' and R", which may be identical or different from each other, represented by hydrogen and an alkyl group having from 1 to 5 carbon atoms, or $R_{12}$ together with $R_{11}$, forms a 4- to 7-membered heterocycle, $R_{13}$ and $R_{15}$, which may be identical or different from each other, may be hydrogen, an alkyl group having from 1 to 5 carbon atoms or an alkoxy group having from 1 to 3 carbon atoms, $R_{14}$ may be hydrogen, an alkyl group having from 1 to 5 carbon atoms, an aryl group, a heteroaryl group, an alkylaryl group, an alkylheteroaryl group, COR', COOR', CON(R')(R") with R' and R", which may be identical or different from each other, represented by hydrogen and an alkyl group having from 1 to 5 carbon atoms, $X_2$ may be an alkyl group having from 1 to 5 carbon atoms, optionally substituted with one or more alkyl groups having from 1 to 5 carbon atoms or one or more alkoxy groups having from 1 to 3 carbon atoms, $X_3$ may be OH, $NH_2$, NHOH or $NHNH_2$, $R_1$ and $R_2$, which may be identical or different from each other, may be hydrogen, an alkyl group having from 1 to 5 carbon atoms or an alkoxy group having from 1 to 3 carbon atoms, $R_3$, $R_4$ and $R_8$, which may be identical or different from each other, may be hydrogen, an alkyl group having from 1 to 5 carbon atoms, an alkoxy group having from 1 to 3 carbon atoms, a halogen atom, —OH, —N(R')(R"), —N(R')COR", —CN, —CONR'R", —$SO_2NR'R"$, —$SO_2R'$, nitro and trifluoromethyl; with R' and R", which may be identical or different from each other, represented by hydrogen and an alkyl group having from 1 to 5 carbon atoms, $R_5$ may be hydrogen, an alkyl group having from 1 to 5 carbon atoms, an alkoxy group having from 1 to 3 carbon atoms, a halogen atom, —OH, —N(R')(R"), —N(R')COR", nitro and trifluoromethyl, or $R_5$ together with one from among $R_6$ and $R_7$ forms a ring having 5 or 6 carbon atoms; with R' and R", which may be identical or different from each other, represented by hydrogen and an alkyl group having from 1 to 5 carbon atoms, $R_6$ and $R_7$, which may be identical or different from each other, may be hydrogen, an alkyl group having from 1 to 5 carbon atoms, or together form a group C=O, or one from among $R_6$ and $R_7$, together with $R_5$, forms a ring having 5 or 6 carbon atoms, $R_{16}$ is an alkyl group having from 1 to 5 carbon atoms, X is a leaving group, Z is I, Br, or Cl.

In an embodiment, X is Br or Cl.

In an embodiment, Z is I; and A is —$C(CH_3)_2$—.

In an embodiment, Z is I; A is —$C(CH_3)_2$—, Y is OH, and $Y_1$ is —$OR_{13}$.

In an embodiment, Z is I; A is —$C(CH_3)_2$—, Y is OH, and $Y_1$ is methoxy or ethoxy.

In another aspect, the present invention provides of a process of making the compound of Formula (XVI)

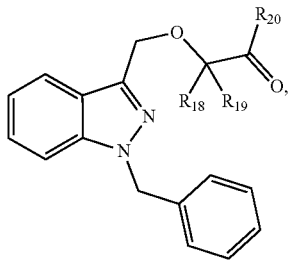
(XVI)

The process comprising: reacting the compound of Formula (XVII)

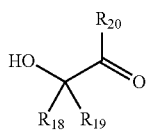
(XVII)

in the presence of $(R_{16})_4NZ$ with the compound of Formula (VI)

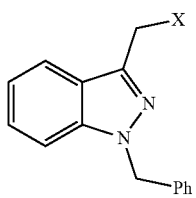
(VI)

to form the compound of Formula (XVI);
wherein $R_{18}$, $R_{19}$, $R_{20}$ each is independently H or an alkyl group having from 1 to 6 carbon atoms,
X is a leaving group,
Z is I, Br, or Cl.

In an embodiment, $R_{18}$, $R_{19}$, $R_{20}$ each is H, methyl, ethyl, isopropyl, butyl, or tert-butyl.

In an embodiment, X is Br or Cl.

In another aspect, the present invention provides of a process of making the compound of Formula (IV)

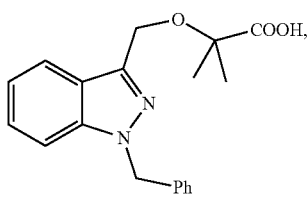
(IV)

The process comprising: reacting the compound of Formula (V)

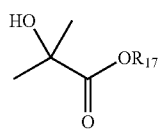
(V)

in the presence of $(R_{16})_4NZ$ with the compound of Formula (VI)

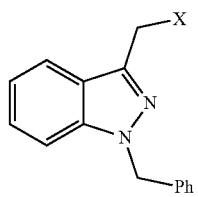
(VI)

to form the compound of Formula (IV);
wherein $R_{16}$, $R_{17}$ each is independently an alkyl group having from 1 to 5 carbon atoms,
X is a leaving group,
Z is I, Br, or Cl.

In an embodiment, $R_{17}$ is methyl, ethyl, isopropyl, butyl, or tert-butyl.

In an embodiment, X is Br or Cl.
In an embodiment, Z is I.
In an embodiment, Z is I; $R_{16}$ is n-butyl; and $R_{17}$ is methyl.

When the compounds of Formula (V) and Formula (VI) react with each other, the intermediate of Formula (VII) is generated, and is further hydrolyzed to afford the compound of Formula (IV). In an embodiment, the intermediate of Formula (VII) is not separated or purified; the reaction is carried out in a one pot reaction. In an embodiment, the intermediate of Formula (VII) is separated and purified, and is further hydrolyzed to afford the compound of Formula (IV).

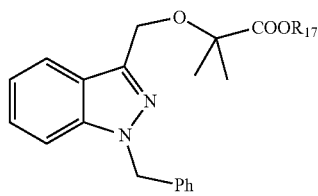
(VII)

In an embodiment, the reaction described herein is carried out in the presence of a base. In an embodiment, the base is selected from the group consisting of alkali metal hydrides, alkali metal alkoxides, alkali metal hydroxides, alkali metal oxides, alkali metal carbonates, quaternary ammonium alkoxides, quaternary ammonium hydroxides, quaternary phosphonium alkoxides, quaternary phosphonium hydroxides, tertiary amines and combinations thereof. The base is selected from the group consisting of NaH, DBU, NaOH, KOH, CsOH, trialkyl amine, pyridine, $K_2CO_3$, IPEA, NaHMDS, ammonia, ammonium hydroxide, and combinations thereof.

In an embodiment, the reaction is described herein carried about at a temperature of about 0-5° C., 20-30° C., about 40-50° C., about 50-60° C., about 60-70° C., or about 70-80° C., In an embodiment, the reaction described herein is carried out in a solvent selected from THF, DMF, acetone, ACN, 2-methyltetrahydrofuran, 2,5-dimethyltetrahydrofuran, N-methylpyrrolidin-2-one, dimethyl sulfoxide, propionitrile, isobutyronitrile, acrylonitrile, ethyl acetate, methyl acetate, methyl formate, butyl formate, rac-1,2-dichloropropane, hexamethylphosphoric triamide, 2-methylanisole, 2-nitropropane, butan-2-one, nitromethane, oxolane, and combinations thereof.

Development of the New Processes

The current art of making 2-((1-benzyl-1H-indazol-3-yl)methoxy)-2-methylpropanoic acid and its derivatives, described in the art WO 2011/015501, does not generate the desired product.

According to the procedure described in WO 2011/015501, the compound of Formula (VIII) was deprotonated with 60% NaH using a mixture of toluene and DMF as solvents. The temperature for this deprotonation was not specified. After deprotonation, a solution of the compound of Formula (XI) in toluene and DMF was added to the deprotonated Formula (VIII). The reaction mixture was then heated to 90° C. for about 10 hours. The reaction was worked up by washing the organic phase with acidic water and then water. After removing solvents, the product was obtained as an oil and was used in the next step as is. The next step was the hydrolysis which was effected using 10 M NaOH (3.1 eq) at refluxing temperature for about 3 hours. The final product was precipitated out from the reaction mixture by adjusting the pH and then filtering, but was found to be the compound of Formula (X).

Due to the deficiency of the procedure described in WO 2011/015501, the procedure described in WO 2011/015501 was modified, first by generating the anion of the compound of Formula (VIII) (in toluene+DMF) at ambient temperature for 0.5 h using NaHMDS (40% in THF) and then treating with the compound of Formula (XI) (in toluene+DMF). Monitoring the progress of the reaction using UPLC showed that the conversion was complete after 1-2 hours at ambient temperature. When the reaction was worked up, it was found that there was no desired product isolated. The only product that was found was the compound of Formula (X) as characterized by 1H-NMR and LC-MS. The hypothesized mechanism of forming the compound of Formula (X) is illustrated below.

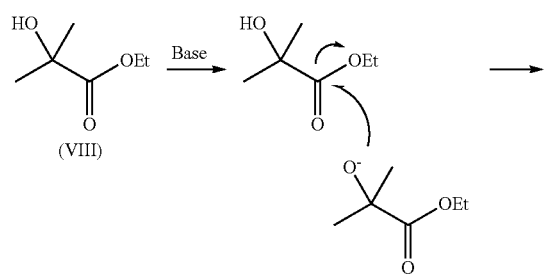

(VIII)

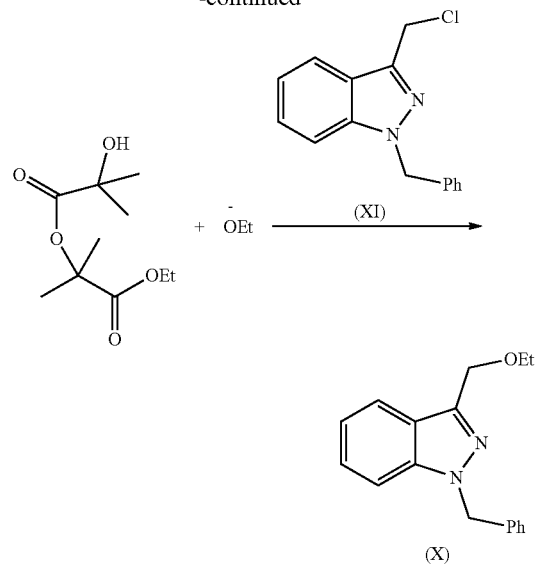

Using NaH as base as per the procedure in WO 2011/015501 was also tried without success, as it gave the same ether product (Formula (X)) as using NaHMDS. Trying to slow down the self coupling of the compound of Formula (VIII) by using either NaH or NaHMDS as base at low temperature (−20° C.) then reacting with the compound of Formula (XI) also did not work. There was no conversion at −20° C. or ambient temperature. Once the reactions were heated, the major product was the ether (Formula (X)).

Using other bases (DIPEA, DBU and $K_2CO_3$) following the same procedure also did not give the desired product. The major product in these cases, along with other impurities, was the alcohol compound of Formula (XV) and the dimer (the compound of Formula (XII)). These impurities were generated in all reactions at various levels.

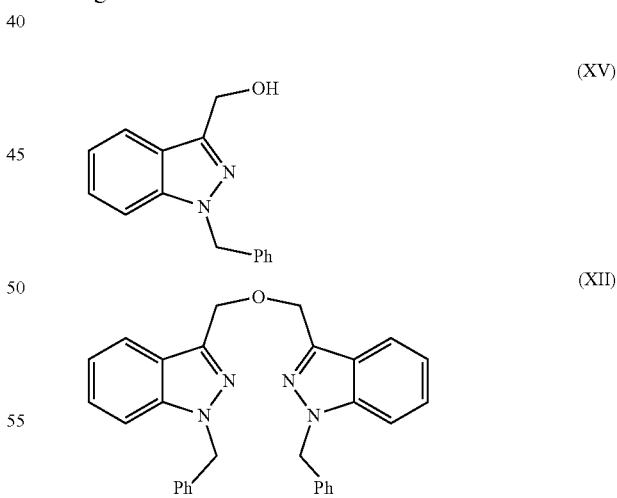

To solve the problems stated above, Applicant developed a new approach to convert the compound of Formula (XI) to a more reactive electrophile. For this purpose, the compound of Formula (XI) was converted to its iodo derivative by agitating at ambient temperature with a slight excess, 1.1 eq. of NaI in acetone for 18 h. Once the reaction was complete, NaCl was filtered off and the filtrate was evaporated to dryness to give 1-benzyl-3-iodomethyl-1H-indazole as the product as confirmed by 1H-NMR and LC-MS. This iodo derivative was used for trial with both NaHMDS and NaH as base and found that it converted to the intermediate Formula (VII) in 1 hour. Interestingly, using $Cs_2CO_3$ as a base, there was no conversion at ambient temperature. At elevated temperature of 40-50° C., the ether compound of Formula (X) was formed. The reaction using NaHMDS as a base could be run using THF or DMF, however, DMF gave cleaner profiles than THF. The synthesis of iodo derivative could be carried out using ACN as solvent although the reaction was slower as after 18 hours at room temperature.

From the knowledge that the iodo derivative would undergo the desired conversion, next approach was to generate this intermediate in situ and use without isolation. The benefit of doing this is twofold. First, it shortens the operation time for preparation. Second, a separate step would need to introduce a new solvent, acetone or ACN. If acetone is used as the solvent, it needs to be completely removed so it does not interfere in the next step. In order to accomplish this in situ preparation, $Bu_4NI$ was used in catalytic amount, 0.26 eq with regards to the compound of Formula (XI) to generate the iodo derivative. It was found that using lower amounts of this catalyst, 0.15-0.18 eq. resulted in higher level of impurities.

In the presence of $Bu_4NI$, a reaction was carried out using NaH as a base in THF. It was found that the reaction was not as clean as using NaHMDS in DMF. The attention was then turned to use NaHMDS (as THF solution) and DMF as the reaction solvent. With this system, it was found that the dimer impurity, the compound of Formula (XII), could be decreased if the generation of alkoxide of Formula (VIII) was done in the absence of the compound of Formula (XI). Originally, it was thought that the generation of alkoxide of Formula (VIII) in the presence of the compound of Formula (XI) would suppress the generation of the ether impurity of Formula (X), but this was not the case. The ether impurity of Formula (X) would be generated with or without the compound of Formula (XI) being present in the reaction mixture from the beginning. The compound of Formula (XII), however, was generated in higher level if the compound of Formula (XI) was present during the alkoxide generation. As such, alkoxide of Formula (VIII) was generated at 0-5° C. for 0.5 hour, then the compound of Formula (XI) with $Bu_4NI$ as a solution in DMF was charged to the alkoxide solution. The reaction was left for a minimum of 10 hours at ambient temperature and found to have more than 99% conversion from the compound of Formula (XI) to the compound of Formula (VII).

In the above stated procedure, the intermediate of the Formula (VII) was isolated by pH adjustment followed by water washes and removal of solvents, and used in the next step as an oil without further purification. As the solvent is DMF which has high boiling point, 153° C., the isolated intermediate would inevitably contain some DMF.

Since the intermediate is likely to be a liquid and cannot be isolated as a solvent free material, the intermediate was used in the hydrolysis reaction without further isolation and purification. In other words, the conversion of the compound of Formula (VIII) to the compound of Formula (IV) was carried out in a one pot reaction. Once the conversion to the compound of Formula (VII) was deemed complete, 1.5 eq of NaOH (50% w/w) was charged to the reaction mixture. After 1.5 hours, it was found that the conversion was complete and the product was tested by LCMS and confirmed to be the desired final product—the compound of Formula (IV). The product was isolated by adjusting the pH of the reaction mixture to pH of 0-1 with concentrated HCl (4 eq), followed by charging water to precipitate out the final product. The solid was collected by filtration, washed with water to remove inorganic salts then with MTBE. The crude product before the MTBE wash had a purity of about 92-95%.

The final product may be further purified by recrystallization using EtOAC, as illustrated in Example 2.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

General Procedures

The compounds of this invention may be made by various methods known in the art. Such methods include those of the following examples, as well as the methods specifically exemplified below. Modifications of such methods that involve techniques commonly practiced in the art of organic synthesis may also be used.

As used herein the symbols and conventions used in these processes, schemes and examples are consistent with those used in the contemporary scientific literature, for example, the *Journal of the American Chemical Society* or the *Journal of Biological Chemistry*. Specifically, the following abbreviations may be used in the examples and throughout the specification:

The following examples describe the invention in further detail, with reference to specific embodiments. These are representative embodiments of the invention which are provided for illustrative purposes only, and which should not be regarded as limiting the invention in any way.

Example 1: Synthesis of 2-((1-benzyl-1H-indazol-3-yl)methoxy)-2-methylpropanoic acid To a dried 3 L three neck round bottle equipped with thermometer, mechanical stirrer, under nitrogen was charged 67.55 g ethyl 2-hydroxy-2-methylpropionate, and 350 mL anhydrous DMF. The solution was cooled to 0-5° C. To the mixture was charged with 233 ml 40% NaHMDS in THF over 30 min. The mixture was agitated at 0-5° C. for 1 h. To a separate flask was charged 100 g 1-benzyl-3-chloromethyl-1H-indazole, 38 g $Bu_4NI$ and 250 mL anhydrous DMF. The mixture was agitated to dissolve. The solution of the second flask was charged to the solution of the first flask while keeping the solution temperature at 0-5° C. The equipment was rinsed forward with 50 ml anhydrous DMF. The mixture was warmed to 20-25° C. and agitated for a minimum of 10 h. The reaction was monitored by UPLC till completion.

Then, to the reaction was charged 30 mL 50% NaOH. The reaction was agitated at 20-25° C. for a minimum of 1 hour. The reaction was monitored by UPLC till completion. Then, The reaction mixture was cooled to 5-10° C. To the reaction mixture was charged 165 mL 36% HCl while keeping the reaction temperature below 25° C. The pH of the reaction mixture was then confirmed to be 0-1. The reaction mixture was then warmed to 20-25° C. To the mixture was charged with 800 mL water over 0.5 hour and agitation continued at 20-25° C. for a minimum of two hours. The product was filtered under nitrogen and was washed with water (4×200 mL) followed by MTBE. The product was dried at 35-40° C. Yield: 62-82% and purity: 95-98%.

Example 2: Purification of 2-((1-benzyl-1H-indazol-3-yl)methoxy)-2-methylpropanoic acid To a 3 L dried three-neck round bottom equipped with thermometer and mechanical stirrer, under nitrogen was charged 525 g of 2-((1-benzyl-1H-indazol-3-yl)methoxy)-2-methylpropanoic acid, made in different batches according to Example 1, and 1575 mL EtOAc. The solution was heated to reflux at 77° C. Then, the solution was filtered through a filter paper and was slowly cooled to 20-25° C. over 2-3 hours and 5-10° C. over 1-2 hour. The mixture was then agitated at 5-10° C. for a minimum of one hour. The product was collected by filtration and washed with pre-chilled EtOAc (2×525 mL). The product was dried at 35-40° C. in the vacuum oven for 18 hours to yield the final product. Purified yield: 88.7% and purity: 99.7%.

We claim:

1. A process of making the compound of Formula (XVI)

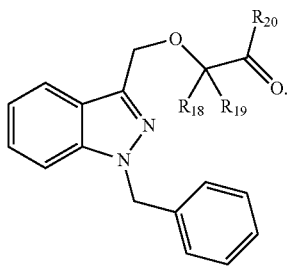

(XVI)

the process comprising: reacting the compound of Formula (XVII)

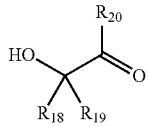

(XVII)

in the presence of $(R_{16})_4NZ$ with the compound of Formula (VI)

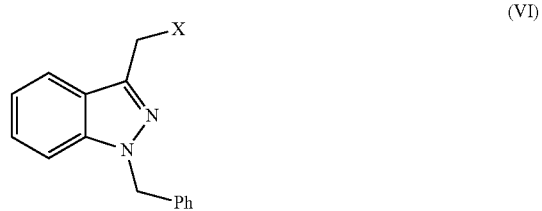

(VI)

to form the compound of Formula (XVI);
wherein $R_{18}$, $R_{19}$, $R_{20}$ each is independently H or an alkyl group having from 1 to 6 carbon atoms,
$R_{16}$ is an alkyl group having from 1 to 5 carbon atoms,
X is a leaving group,
Z is I, Br, or Cl.

2. The process of claim 1, wherein X is Cl or Br.

3. The process of claim 1, wherein the reaction is carried out in the presence of a base.

4. The process of claim 3, wherein the base is selected from NaH, DBU, NaOH, KOH, CsOH, trialkyl amine, pyridine, $K_2CO_3$, IPEA, NaHMDS, ammonia, ammonium hydroxide, and combinations thereof.

5. The process of claim 1, wherein Z is I.

6. The process of claim 1, wherein the reaction is carried out as a one pot reaction.

7. The process of claim 1, wherein the reaction is carried out in a solvent.

8. The process of claim 7, wherein the solvent is selected from THF, DMF, acetone, ACN, 2-methyltetrahydrofuran, 2,5-dimethyltetrahydrofuran, N-methylpyrrolidin-2-one, dimethyl sulfoxide, propionitrile, isobutyronitrile, acrylonitrile, ethyl acetate, methyl acetate, methyl formate, butyl formate, rac-1,2-dichloropropane, hexamethylphosphoric triamide, 2-methylanisole, 2-nitropropane, butan-2-one, nitromethane, oxolane, and combinations thereof.

9. The process of claim 1, wherein each $R_{18}$, $R_{19}$, $R_{20}$ is H, methyl, ethyl, isopropyl, butyl, or tert-butyl.

* * * * *